United States Patent
Al-Zaydi et al.

(10) Patent No.: US 10,280,134 B1
(45) Date of Patent: May 7, 2019

(54) POTENT CYTOTOXIC AGENT AGAINST HUMAN HEPATOCELLULAR CARCINOMA CELL LINE BASED ON 2-ARYL HYDRAZONOPROPANAL PHARMACOPHORE

(71) Applicant: King Abdulaziz University, Jeddah (SA)

(72) Inventors: Khadijah M. Al-Zaydi, Jeddah (SA); Tamer S. Saleh, Jeddah (SA); Taibi Ben Hadda, Oujda (MA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 16/127,932

(22) Filed: Sep. 11, 2018

(51) Int. Cl.
*A61K 45/06* (2006.01)
*A61K 9/127* (2006.01)
*A61P 35/00* (2006.01)
*A61K 31/235* (2006.01)
*C07C 251/74* (2006.01)
*C07D 333/08* (2006.01)

(52) U.S. Cl.
CPC ............ *C07C 251/74* (2013.01); *A61K 9/127* (2013.01); *A61K 31/235* (2013.01); *A61K 45/06* (2013.01); *A61P 35/00* (2018.01); *C07D 333/08* (2013.01)

(58) Field of Classification Search
None
See application file for complete search history.

(56) References Cited

PUBLICATIONS

Al-Zaydi et al., Journal of Chemical Research (S), (2000), 4, pp. 154-155.*
Al-Zaydi et al., Molecules (2003), 8(12), pp. 910-923.*
Al-Zaydi et al., Molecules (2007), 12(8), pp. 2061-2079.*
Yahia Nasser Mabkhot, et al., "Substituted thieno[2,3-b]thiophenes and related congeners: Synthesis, β-glucuronidase inhibition activity, crystal structure, and POM analyses", Bioorganic & Medicinal Chemistry, vol. 22, Issue 23, Dec. 1, 2014, pp. 6715-6725 (Abstract only).
Mahmoud B. El-Ashmawy, et al., "Synthesis, in vitro antitumor activity and DNA-binding affinity of novel thiadiazolopyrimidine and thiadiazoloquinazoline derivatives", Mansoura Journal of Pharmaceutical Sciences, vol. 26, No. 1, 2010, pp. 60-68 (Abstract only).
Hatem M. Gaber. et al., "New Heterocyclic Syntheses from Pyridinethiones: an Efficient Route for the Syntheses of Some Novel Azo Derivatives of Thieno[2,3-b]pyridine as Potential Antibacterial and Anti-cancer Agents", AFINIDAD, vol. 65, No. 533, Jan.-Feb. 2008, pp. 61-72.
Kyun-Hwan Kim, et al., "Pharmacophore-based virtual screening: a review of recent applications", Expert Opinion on Drug Discovery, vol. 5, Issue 3, Mar. 2010, pp. 205-522 (Abstract only).
Riham F. George, et al., "Synthesis and molecular modeling studies of indole-based antitumor agents", RSC Advances, vol. 6, Issue 51, May 4, 2016, pp. 45434-45451 (Abstract only).
Siva S. Panda, et al., "Synthesis and molecular modeling of antimicrobial active fluoroquinolone—pyrazine conjugates with amino acid linkers", Bioorganic & Medicinal Chemistry Letters, vol. 26, 2016, pp. 2198-2205.
Mohamed A. Ibrahim, et al., "Macrocyclic peptidomimetics with antimicrobial activity: synthesis, bioassay, and molecular modeling studies", Organic & Biomolecular Chemistry, vol. 13, 2015, pp. 9492-9503.
Nasser S. M. Ismail, et al., "Rational design, synthesis and 2D-QSAR studies of antiproliferative tropane-based compounds", RSC Advances, vol. 6, 2016, pp. 101911-101923.

* cited by examiner

*Primary Examiner* — Brian J Davis
(74) *Attorney, Agent, or Firm* — Oblon, McClelland, Maier & Neustadt, L.L.P.

(57) ABSTRACT

The invention is directed to 2-aryl hydrazonopropanals that exert anti-tumor activity and methods for using them to prevent, inhibit and treat cancer. It also involves anti-tumor compositions containing these 2-aryl hydrazonopropanals, and methods of treatment using these compositions.

17 Claims, 1 Drawing Sheet

POTENT CYTOTOXIC AGENT AGAINST HUMAN HEPATOCELLULAR CARCINOMA CELL LINE BASED ON 2-ARYL HYDRAZONOPROPANAL PHARMACOPHORE

BACKGROUND

Field of Invention

The invention pertains to the fields of pharmacology and chemistry. The invention relates to 2-aryl hydrazonopropanal compounds that have cytotoxic activity on human hepatocellular carcinoma ("HCC") cells.

Description of Related Art

The "background" description provided herein is for the purpose of generally presenting the context of the disclosure. Work of the presently named inventor(s), to the extent it is described in this background section, as well as aspects of the description which may not otherwise qualify as prior art at the time of filing, are neither expressly or impliedly admitted as prior art against the present invention.

Hepatocellular carcinoma (HCC) is the third most common cause of cancer death, the most recurrent primary liver cancer and the fifth most common malignancy worldwide with over 700,000 new cases per year. Although the incidence of HCC is steadily rising worldwide, 25% of patients only benefit from curative treatment; Alves R C, Alves D, Guz B, et al. *Advanced hepalocellular carcinoma. Review of targeted molecular drugs*. Ann Hepatol 2011; 10:21.

Furthermore, most patients seek treatment when the disease is beyond curative treatment (surgery or percutaneous ablation), and palliative care is the only alternative; Bosch F X, Ribes J, Diaz M, Cléries R. *Primary liver cancer: worldwide incidence and trends*. Gastroenterology 2004; 127:5-16; Whittaker S, Marais R, Zhu A X. *The role of signaling pathways in the development and treatment of hepatocellular carcinoma*. Oncogene 2010:29:4989-5005.

The treatment of patients with HCC presents a major challenge, because associated cirrhosis limits the choice of chemotherapeutic agents. The possible therapeutic options fall into five main categories: (i) surgery, including tumor resection and liver transplantation; (ii) percutaneous interventions, including ethanol injection, cryoablation, and radiofrequency thermal ablation; (iii) transarterial interventions, including embolization and chemoembolization; (iv) radiation therapy, and (v) gene and immune therapeutic drugs; Blum H E. *Hepatocellular carcinoma: therapy and prevention*. World J Gastroenterol 2005; 11:7391-400.

Although treatment options have become more diverse in recent years, improvements in HCC survival rates lag far behind those achieved in other tumors. Until recently, no real therapy existed for patients with advanced HCC. Systemic chemotherapy in particular has been disappointing, not only because of the chemoresistance of HCC, but also of major side effects which make them poorly tolerated by patients with liver cirrhosis; Whittaker S, Marais R, Zhu A X. The role of signaling pathways in the development and treatment of hepatocellular carcinoma. Oncogene 2010:29:4989-5005. The management of HCC is dictated by the degree of underlying liver dysfunction, the burden of malignancy and the patient's performance status. In contrast to the early-stage HCC, there are limited treatment options for advanced HCC. In this context, several therapeutic agents have been developed over the past 50 years in order to provide a better response and improve the survival of HCC patients; Rutman R J, Cantarow A, Paschkis K E. *Studies in 2-acetylaminofluorene carcinogenesis. 1. The intracellular distribution of nucleic acids and protein in rat liver*. Cancer Res 1954; 14:111-4; Kaseb A O, Shindoh J, Patt Y Z, et al., *Modified cisplatin/interferon alpha-2b/doxorubicin/5-fluorouracil [PIAF]chemotherapy in patients with no hepatitis or cirrhosis is associated with improved response rate, resectability, and survival of initially unrespectable hepatocellular carcinoma*. Cancer 119:3334-42 (2013); Yang T S, Lin Y C, Chen J S, et al., *Phase II study of gemcitabine in patients with advanced hepatocellular carcinoma*. Cancer 2000; 89(4):750-6 (2014).

Moreover, different modulation strategies and administration routes have been proposed to enhance the antitumor activity of these agents; Hung C S, Lin S F, Liu H H, et al. *Survivin-mediated therapeutic efficacy of gemcitabine through glucose-regulated protein 78 in hepatocelhdular carcinoma*. Ann Surg Oncol 2012; 19:2744-52; Li T, Dong Z R, Guo Z Y, et al. *Aspirin enhances IFN-alpha-induced growth inhibition and apoptosis of hepatocellular carcinoma via JAK1/STAT1 pathway*. Cancer Gene Ther 2013; 20:366-74; Song D S, Bae S H, Song M J, et al. *Hepatic arterial infusion chemotherapy in hepatocellular carcinoma with portal vein tumor thrombosis*. World J Gastroenterol 2013; 19:4679-88; Kodama Y, Fumoto S, Nishi J, et al., *Absorption and distribution characteristics of 5-fluorouracil [5-FU] after an application to the liver surface in rats in order to reduce systemic side effects*. Biol Pharm Bull 2008; 31:1049-52.

Chemotherapeutic agents used to treat hepatocellular carcinoma treatment include Sorafenib (which inhibits several tyrosine protein kinases such as VEGFR, PDGFR and Raf family kinases and can induce autophagy), 5-fluorouracil (an antimetabolite that may block action of thymidylate synthase and stop DNA production), doxorubicin (which intercalates with DNA and disrupts DNA replication and repair) as well as Regorafenib (Stivarga®, which inhibits several kinases such as VEGFR-1, VEGFR-2 and VEGFR-3). FIG. 1 shows the chemical structures of some of these drugs.

Administration of doxorubicin, which is used to treat HCC and other cancers, induces the formation of reactive oxygen species ("ROS"), oxidative stress, and triggering of apoptosis and cell death; Minotti G, Recalcati S, Mordente A, et al., *The secondary alcohol metabolite of doxorubicin irreversibly inactivates aconitase/iron regulatory protein-1 in cytosolic fractions from human myocardium*. FASEB J 1998; 12:541-52; Miyamoto Y, Koh Y H, Park Y S, et al., *Oxidative stress caused by inactivation of glutathione peroxidase and adaptive responses*. Biol Chem 2003; 384:567-74; Wang S, Kotamraju S, Konorev E, et al., *Activation of nuclear factor-kappaB during doxorubicin-induced apoptosis in endothelial cells and myocytes is pro-apoptotic: the role of hydrogen peroxide*. Biochem J 2002; 367:729-40.

A relatively new cytotoxic drug for HCC treatment is Sorafenib. However, resistance to Sorafenib has been reported and is attributed to its broad spectrum kinase inhibition and induction of mammalian target of rapamycin (mTOR)-dependent autophagy; Chen K F, Chen H L, Tai W T, Feng W C, Hsu C H, Chen P J, Cheng A L., *Activation of phosphatidylinositol 3-kinase/Akt signaling pathway mediates acquired resistance to sorafenib in hepatocellular carcinoma cells*. J Pharmacol Exp Ther. 2011; 337:155-161.

Other anti-cancer drugs may be used to treat HCC. The majority of drugs used for the treatment of cancer today are cytotoxic or cell-killing drugs that work by interfering in some way with the operation of a cell's DNA; Munoz, N.;

Bosch, F. X., de Sanjose, S., Shah, K. V. Mutat. Res. 1994, 305, 293. However, a dose of a cytotoxic drug sufficient to kill tumor cells is also often toxic to normal tissues and can trigger undesired side effects. The lack of sufficient cancer-cell-specific cytotoxicity and side effects limit treatment of HCC and other cancers with these drugs, for example, 5-fluorouracil ("5-FU") is an anticancer drug that has a very short half-life in the body and is therefore administered in multiple doses to maintain a therapeutic blood level. However, the effects of continuously maintaining a therapeutic level of 5-FU in the blood include severe side effects such as gastrointestinal toxicity and hematologic and bone marrow disorders; Kodama Y, Fumoto S, Nishi J, et al. *Absorption and distribution characteristics of 5-fluorouracil [5-FU] after an application to the liver surface in rats in order to reduce systemic side effects*. Biol Pharm Bull 2008; 31:1049-52.

To overcome or avoid problems with conventional anticancer drugs, many different strategies are being used. These include (i) chemical modification of a drug; (ii) co-administration of chemosensitizing compounds generally acting as P-gp inhibitors; (iii) the use of drug carriers such as microspheres, liposomes, or nanoparticles; and (iv) evaluation of novel synthetic compounds as cytotoxic compounds; Tapiero H, Mishal Z, Wioland M, Silber A, Fourcade A, Zwingelstein G., *Changes in biophysical parameters and in phospholipid composition associated with resistance to doxorubicin*. Anticancer Res 1986; 6:649-652; Kellen J A. *The reversal of multidrug resistance in cancer* (review). Anticancer Res 1993; 13:959-961; Brigger I, Dubernet C, Couvreur P., Nanoparticles in cancer therapy and diagnosis. Adv Drug Deliv Rev 2002; 54:631-651.

In view of the limitations of conventional drugs used for treating HCC, the inventors sought to identify new cytotoxic agents that are safe and efficacious. Based on their prior work synthesizing 2-aryl hydrazonopropanals described by Al-Zaydi K. M., Borik R. M. Microwave *Assisted Condensation Reactions of 2-Aryl Hydrazonopropanals with Nucleophilic Reagents and Dimethyl Acetylenedicarboxylate*, Molecules 2007, 12, 2061-2079, the inventors sought to determine whether 2-aryl hydrazonopropanals would exhibit inhibitory or cytotoxic effects on hepatocellular carcinoma or HCC cells.

BRIEF SUMMARY OF THE INVENTION

The invention relates to cytotoxic compounds that inhibit or kill human hepatocellular carcinoma cell line. Embodiments include 2-aryl hydrazonopropanals that exhibit cytotoxicity against HCC. The cytotoxic compounds of the present disclosure conform to formula I:

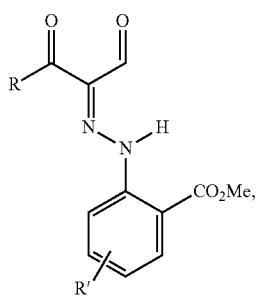

wherein R is alkyl, alkenyl, or alkynyl, which may be unsubstituted or substituted, for example, with halo (e.g., F, Cl, Br, etc.), hydroxy (—OH) or amino ($NH_2$); or aryl or a 5- or 6-membered hetero-ring, each of which may be unsubstituted or substituted, for example, with $C_1$-$C_6$ alkyl, halo (e.g., F, Cl, Br, etc.), hydroxy (—OH) or amino ($NH_2$). Preferably R is $C_1$-$C_6$ alkyl, alkenyl, or alkynyl; or aryl or thienyl. R' is hydrogen or unsubstituted or substituted alkyl, alkenyl, alkynyl or aryl.

Examples of such cytotoxic compounds include:

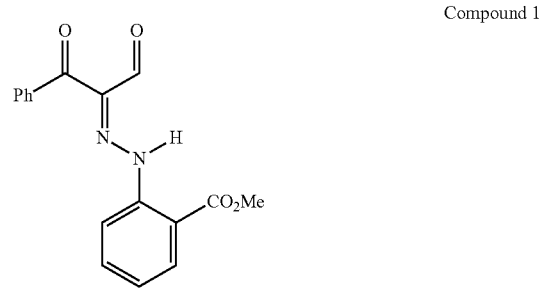

Compound 1

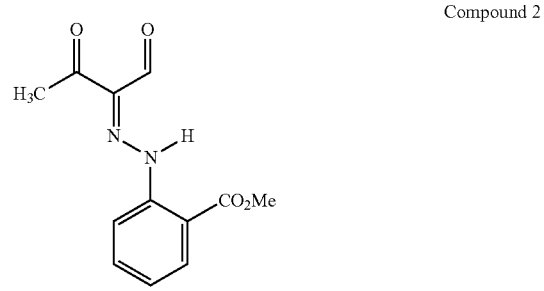

Compound 2

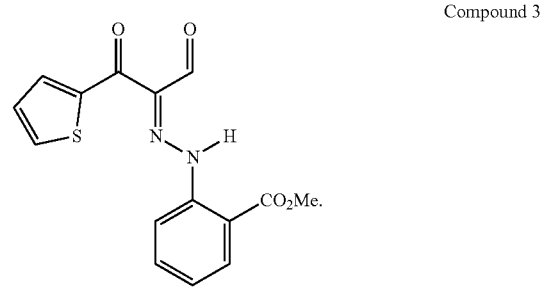

Compound 3

It was found that these compounds show excellent inhibitory effect as compared to reference antitumor drug compound doxorubicin (adriamycin). Moreover, Compound 1 was determined to be substantially safe when administered to a normal human epithelial cell line.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
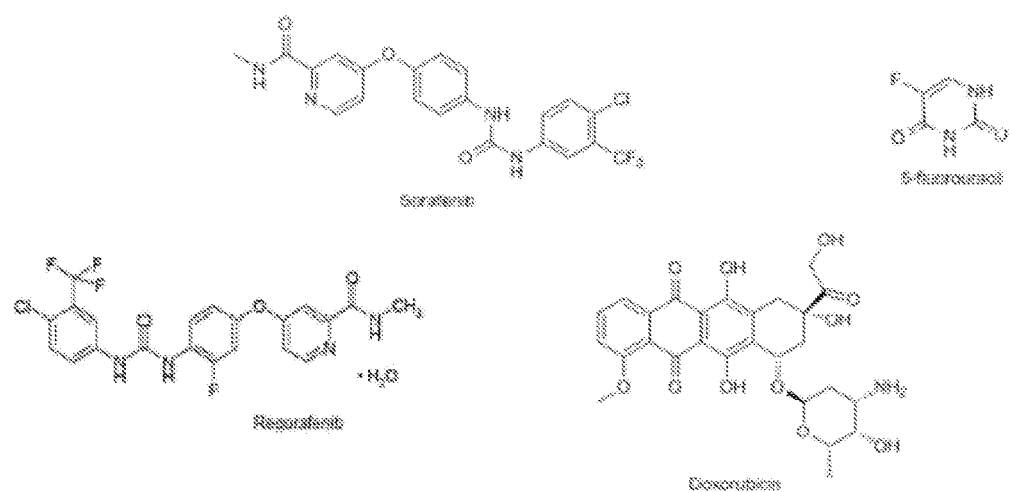
FIG. 1. Chemical structures of Sorafenib (CAS: 284461-73-0), Regorafenib (CAS: 755037-03-7), 5-fluorouracil, and doxorubicin.
Figure 2:
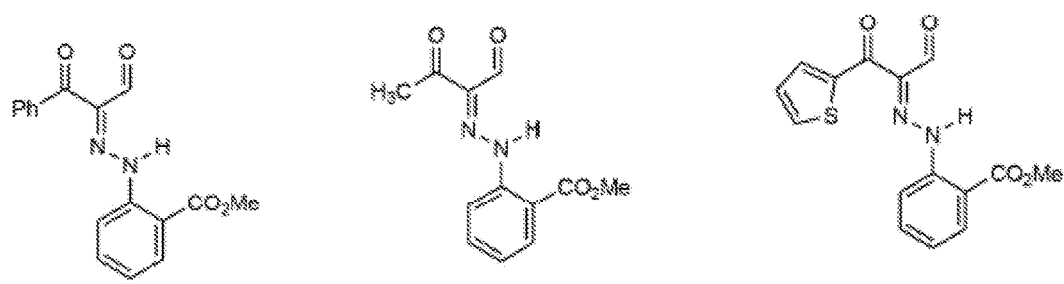
FIG. 2. Chemical structures of Compounds 1, 2 and 3.

HCC Staging.

Staging systems help prognose patients with cancer, stratify patients according medical specialists and researchers, and guide the therapeutic approach. Various staging systems for HCC are used including those described by Pons, et al., HPB (Oxford). 2005, 7(1):35-41 which is incorporated by reference. Administration of a compound according to the invention may take place during one or more stages of disease or to patients at different stages of disease including early HCC, intermediate-advanced HCC, and end-stage HCC.

Chemotherapy.

The 2-aryl hydrazonopropanal compounds or compositions containing them, such as liposomes or liposomes with PEGylated components, may be administered to subjects having HCC or at risk of developing or relapsing from HCC. They may be administered by routes known in the art, preferably parenterally such as by intravenous infusion. In some embodiments, a compound of the invention will be targeted to HCC or other cancer cells by formulation with one or more ligands that bind to tumor cells, such as by ligands that bind to tumor associated antigens. In other embodiments, the biological half-life of a compound of the invention may be extended compared to a corresponding unmodified compound, by modification (e.g., PEGylation) or formulation into a nanoparticle such as a liposome. A drug, protein, peptide or other component of a therapeutic composition may be PEGylated; see Drug Discov Today. 2005 Nov. 1; 10(21):1451-8 (incorporated by reference). Such modifications are used to alter other pharmacokinetic properties such as solubility of a composition containing a compound of the invention or its ability to deliver the compound of the invention into a cell.

Typically, a cytotoxic amount of a compound of the invention is administered. A dosage regimen may be determined by one skilled in the art based on patient status including sex, and age, genetic background, medical history, location and stage of cancer or other condition being treated, and prognosis. Dosage may be based on a cytotoxic amount determined in vitro, for example, on an amount that would expose cancer cells in vivo to a concentration of a 2-aryl hydrazonopropanal that kills 1, 2, 5, 10, 15, 20, 25, 30, 35, 40, 45, 50, 55, 60, 65, 70, 75, 80, 90, 95% or more tumor cells in vitro. In some embodiments, a dosage will be selected that delivers about 0.1, 0.2, 0.5, 1, 2, 5, 10, 15, 20, 25, 30, 35, 40, 45, 50, 55, 60, 65, 70, 75, 80, 90, 95, 100, 110, 120, 150, 130, 140, 150, 160, 170, 180, 190, 200 or more μg/ml to, around, or into HCC or other target cells. These ranges include all intermediate values and subranges. Dosages may also be calculated using guidelines as described by Gurney, H, British J. Canc. 86:1297-1302 (2002), incorporated by reference.

Preferably, the 2-aryl hydrazonopropanal is administered parenterally, such as by i.v. infusion or injection. Another preferred mode is direct injection into tissue or mass containing HCC. A treatment that targets a cytotoxic 2-aryl hydrazonopropanal to, around, or into HCC or other target cells is advantageous as it reduces exposure of normal cells to high concentrations (relative to those in or around HCC cells) of 2-aryl hydrazonopropanal. Compositions or formulations for parenteral administration can be in the form of aqueous or non-aqueous isotonic sterile injection or infusion solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. For some diseases, disorders or conditions, nonparenteral modes of administration may be used such as by oral or topical administration of a compound of the invention.

As used herein, a "pharmaceutically acceptable carrier" refers to a carrier or diluent that does not cause significant irritation to an organism, does not abrogate a biological activity and properties of a compound of the invention when therapeutically administered, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations which can contain a compound according to the invention is described in, e.g., Remington's Pharmaceutical Sciences, 21st Edition, ed. University of the Sciences in Philadelphia, Lippincott, Williams & Wilkins, Philadelphia Pa., 2005, which is incorporated herein by reference in its entirety.

Adjunct Therapy.

Conventional drugs used to treat HCC include doxorubicin and Sorafenib as well as those drugs described in the Background. In some embodiments a compound according to the invention is used in combination with one or more other modes of HCC treatment, including surgery, radiation therapy, immunotherapy and conventional chemotherapies. In some embodiments, a compound of the invention may be used in combination with a P-gp inhibitor. These inhibit the function of P-glycoprotein 1 (permeability glycoprotein, abbreviated as P-gp or Pgp) also known as multidrug resistance protein 1 (MDR1) or ATP-binding cassette subfamily B member 1 (ABCB1) or cluster of differentiation 243 (CD243). P-gp is an important protein of the cell membrane that pumps foreign substances out of cells. It is an ATP-dependent efflux pump with broad substrate specificity. It exists in animals, fungi and bacteria and may have evolved as a defense mechanism against harmful substances. Some common pharmacological inhibitors of P-glycoprotein include: amiodarone, clarithromycin, ciclosporin, colchicine, diltiazem, erythromycin, felodipine, lansoprazole, omeprazole and other proton-pump inhibitors, nifedipine, paroxetine, sertraline, quinidine, tamoxifen and verapamil; Srivalli, K M R; Lakshmi, P K (July 2012). "*Overview of P-glycoprotein inhibitors: a rational outlook*". Brazilian Journal of Pharmaceutical Sciences. 48 (3): 353-367.

A drug carrier is any substrate used in the process of drug delivery which serves to improve the selectivity, effectiveness, and/or safety of drug administration. Drug carriers are primarily used to control the release of a drug into systemic circulation. This can be accomplished either by slow release of the drug over a long period of time (typically diffusion) or by triggered release at the drug's target by some stimulus, such as changes in pH, application of heat, and activation by light. Drug carriers are also used to improve the pharmacokinetic properties of many drugs with poor water solubility and/or membrane permeability, such as bioavailability. A wide variety of drug carrier systems may be used in conjunction with the invention, each of which has unique advantages and disadvantages. Some of the more popular types of drug carriers include liposomes, polymeric micelles, microspheres, and nanoparticles; Svenson, Sönke (2004). *Carrier-Based Drug Delivery*. Washington, D.C.: American Chemical Society. ISBN 9780841238398. A compound according to the invention may be attached to a carrier in different ways such as by adsorption, integration into a bulk structure, encapsulation, or covalent bonding.

PEGylation is a process of covalent or non-covalent attachment or amalgamation of polyethylene glycol polymer chains to molecules and macrostructures, such as a drug, therapeutic protein or vesicle, which is then described as PEGylated (pegylated). A drug, carrier, targeting moiety, or other molecule may be PEGylated by incubating it with a reactive derivative of PEG. Covalent attachment of PEG to a pharmaceutical compound can mask the compound from a host's immune system and increase the hydrodynamic size (size in solution) of the compound which prolongs its circulatory time by reducing renal clearance. PEGylation can also provide water solubility to hydrophobic pharmaceuticals. In some embodiments, a compound of the invention is incorporated into a PEGylated liposome or other nanoparticle which may contain PEGylated components; Jain, et al., Curr Mol Med. 2018 Apr. 15. doi: 10.2174/1566524018666180416101522 (incorporated by reference). The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, tyrosine. The N-terminal amino group and the C-terminal carboxylic acid can also be used as a site specific site by conjugation with aldehyde functional polymers. Liposomes may be PEGylated in a similar manner to those containing doxorubicin; see Rose, The Oncologist, March 2005, vol. 10 (3), pp. 205-214 (incorporated by reference).

A liposome is a spherical vesicle having at least one lipid bilayer. The liposome can be used as a vehicle for administration of a pharmaceutical drug. Liposomes can be prepared by disrupting biological membranes (such as by sonication). Liposomes are most often composed of phospholipids, especially phosphatidylcholine, but may also include other lipids, such as egg phosphatidylethanolamine, so long as they are compatible with lipid bilayer structure. A liposome design may employ surface ligands for attaching to unhealthy tissue. The major types of liposomes are the multilamellar vesicle (MLV, with several lamellar phase lipid bilayers), the small unilamellar liposome vesicle (SUV, with one lipid bilayer), the large unilamellar vesicle (LUV), and the cochleate vesicle. Liposome delivery systems such as small unilamellar vesicles, large unilamellar vesicles and multilamellar vesicles may also be employed as delivery means for the compounds of the invention. Liposomes may be formed from a variety of phospholipids such as cholesterol, stearylamine and phosphatidylcholines. In some embodiments, a composition of the invention will be in the form of a liposome containing a compound of the invention and optionally a targeting moiety, a detectable moiety, or other anticancer agent(s).

Nanoparticles and Other Compositional Forms.

A compound of the invention may also be incorporated into a nanoparticle, such as particles having average diameters ranging from at least 1, 10, 20, 30, 40, 50, 60, 70, 80, 90, or 100 nm. A compound of the invention may also be incorporated into a micelle, conjugated to a dendrimer, nanosphere, incorporated into a nanocapsule or associated with other nanoscale carriers.

Targeting Moieties.

A compound of the invention, which may be in the form of a liposome or nanoparticle, may be covalently or non-covalently associated with at least one targeting moiety. These include antibodies, antibody fragments, peptides, small molecules, aptamers, nucleic acids, and other ligands that bind to tumor-associated antigens, as well as targeting moieties, and linkers and bioconjugation methods, described by and incorporated by reference to Steichen, et al., Eur. J. Pharm. Sci. 48:416-427 (2013); and Yu, et al., Theranostics 2(1):3-44 (2012).

Imaging Materials.

A compound of the invention may also be covalently or non-covalently associated with one or more imaging moieties including magnetic iron oxide nanoparticles, aptamers, nucleic acids, or fluorescent dyes; Yu, et al., Theranostics 2(1):3-44 (2012, incorporated by reference).

Embodiments. Nonlimiting Embodiments of the Invention Include

A 2-aryl hydrazonopropanal, or an amount or form thereof that prevents or treats HCC or inhibits viral replication or spread, includes compounds of formula I:

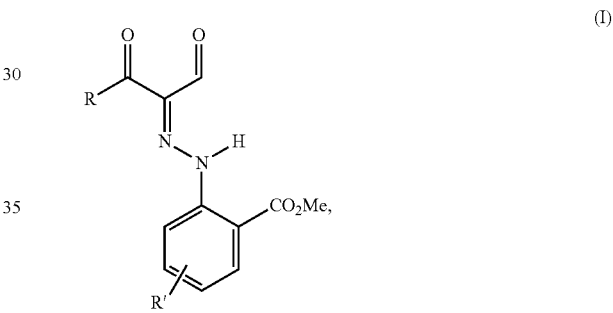

wherein R is unsubstituted or substituted alkyl, alkenyl, alkynyl, aryl, or a 5- or 6-membered ring containing at least one nitrogen, oxygen or sulfur atom. In some embodiments, R in formula I above is methyl, ethyl, n-propyl, isopropyl, n-butyl, s-butyl, t-butyl, isobutyl, pentyl or hexyl or other saturated or unsaturated hydrocarbyl. R may contain 1, 2, 3, 4, 5, 6 carbon atoms. In other embodiments, R may be cycloalkyl or aryl, such as $C_3$-$C_7$ cycloalkyl, phenyl, methylbenzyl, dimethylbenzyl, or naphthyl. In other embodiments, R may be a 5- or 6-membered hetero-ring containing O, N or S, such as thienyl or 2-thienyl. In some embodiments, R may be further substituted with $C_1$-$C_6$ alkyl, $C_1$-$C_6$ alkenyl or $C_1$-$C_6$ alkynyl, hydroxy, amino, a primary, secondary or tertiary amine, or halo, such as F, Cl or Br. In other embodiments, R may be H, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, or an optionally substituted hydrocarbyl. Preferably, R is $C_1$-$C_6$ alkyl, phenyl or thienyl.

R' is hydrogen or unsubstituted or substituted alkyl, alkenyl, alkynyl or aryl.

In some embodiments, a compound of the invention may be contained in a PEGylated composition such as inside of or attached to a nanoparticle, such as a liposome that is PEGylated. A carrier may be selected to improve the pharmacokinetics of the compound of the invention including biological half-life, biocompatibility, and targeting to a cancer or tumor site.

Another embodiment is directed to a pharmaceutical composition containing a compound according to the invention, such as that described by Formula I, and at least one pharmaceutically acceptable carrier, excipient or solvent. Such a composition may be in the form of a liposome or it may contain a modified form of the compound of the invention, such as those modified forms described above. A composition according to the invention may also further contain another anti-tumor or anti-cancer drug or agent, a targeting agent, or a detectable tag or moiety.

Another embodiment of the invention is directed to a method for preventing or treating a disease, disorder or condition associated with abnormal or aberrant cellular proliferation, such as hepatocellular carcinoma ("HCC") by administering a compound of the invention to a subject in need thereof, such as a subject having HCC or at risk of developing HCC, or who is in remission from HCC. This embodiment of the invention may be performed by itself or in conjunction with one or more other therapies, such as by surgical resection or removal of the abnormal, aberrant or cancerous cells, radiation treatment, chemotherapy, immunotherapy, or targeted anticancer therapy. A patient, such as one having HCC or at risk of developing HCC may be concurrently treated for hepatitis B or hepatitis C, alcoholism or cirrhosis or the liver, or for obesity, diabetes, Type II diabetes, an iron storage disease, or exposure to aflatoxin or other hepatotoxins. Patients at risk of HCC may also be treated. These include patients having hemochromatosis, alpha 1-antitrypsin deficiency, Wilson's disease, hemophilia, metabolic syndrome and non-alcoholic fatty liver disease ("DASH"). Children with biliary atresia, infantile cholestasis, glycogen-storage diseases, and other cirrhotic diseases of the liver are predisposed to developing HCC in childhood and may be treated.

EXAMPLE

The following example illustrates various aspects of the present invention. It is not to be construed to limit the claims in any manner whatsoever.

Synthesis.

The inventors have previously described synthesis of the E-methyl 2-(2-(1,3-dioxo-1-phenylpropan-2-ylidene)hydrazinyl)benzoate, which is incorporated by reference; Al-Zaydi K. M., Borik R M. *Microwave Assisted Condensation Reactions of 2-Aryl Hydrazonopropanals with Nucleophilic Reagents and Dimethyl Acelylenedicarboxylate, Molecules*, 2007, 12, 2061-2079. Such a method may be used to produce the 2-aryl hydrazonopropanal compounds of the invention.

Synthesis involves a coupling reaction between the aryl diazonium salt and enaminone in which a cold solution of aryldiazonium salt (10 mmol) was prepared by adding a solution of sodium nitrite (1 g in 10 mL $H_2O$) to a cold solution of aryl amine hydrochloride (10 mmol of aryl amine in 5 mL concentrated HCl) with stirring. The resulting solution of the aryldiazonium salt was then added to a cold solution of enaminone in EtOH (50 mL) containing sodium acetate (1 g in 10 mL $H_2O$). The mixture was stirred at room temperature for 1h and the solid product thus formed was collected by filtration and crystallized from the appropriate solvent.

Cytotoxic Activity.

Cytotoxic activities of test compounds were assessed by an in vitro bioassay on human tumor cells and determined by the Bioassay-Cell Culture Laboratory, National Research Centre, El-Tahrir St., Dokki, Cairo 12622, Egypt. The activity of the test compounds on a non-cancerous, normal human fibroblast cell line, BJ1, was assessed by the mitochondrial dependent reduction of yellow MTT (3-(4,5-dimethylthiazol-2-yl)-2,5-diphenyl tetrazolium bromide) to purple formazan; Mosmann T. *Rapid colorimetric assays for cellular growth and survival: Application to proliferation and cytotoxicity assays*. J Immunol Methods. 1983; 65:55-63.

All procedures were done in a sterile area using a Laminar flow cabinet biosafety class II level (Baker, SG4031NT, Sanford, Me., USA). Cells were suspended in RPMI 1640 medium for HePG2, MCF7 and HCT116 and DMEM for A549 and PC3, 1% antibiotic-antimycotic mixture (10,000 U/ml Potassium Penicillin, 10,000 µg/ml Streptomycin Sulfate and 25 µg/ml Amphotericin B) and 1% L-glutamine at 37° C. under 5% $CO_2$.

Cells were batch cultured for 10 days, then seeded at concentration of $10 \times 10^3$ cells/well in fresh complete growth medium in 96-well microtiter plastic plates at 37° C. for 24 h under 5% $CO_2$ using a water jacketed Carbon dioxide incubator (Sheldon, TC2323, Cornelius, Oreg., USA). Media was aspirated, fresh medium (without serum) was added and cells were incubated either alone (negative control) or with different concentrations of sample to give a final concentration of 100, 50, 25, 12.5, 6.25, 3.125, 1.56 and 0.78 µg/ml. After 48 h of incubation, medium was aspirated, 40 µl MTT salt (2.5 µg/ml) were added to each well and incubated for further four hours at 37° C. under 5% $CO_2$. To stop the reaction and dissolving the formed crystals, 200 µL of 10% Sodium dodecyl sulphate (SDS) in deionized water was added to each well and incubated overnight at 37° C.

A positive control which composed of 100 µg/ml was used as a known cytotoxic natural agent who gives 100% lethality under the same conditions; Thabrew M. I., Hughes R. D., McFarlane I. G. *Screening of hepatoprotective plant components using a HepG2 cell cytotoxicity assay*, J Pharm Pharmacol. 1997, 49:1132-5.22; El-Menshawi B. S., Fayad W., Mahmoud K., El-Hallouty S. M., El-Manawaty M., Olofsson M. H., Linder S., *Screening of natural products for Therapeutic activity against solid tumors, Indian Journal of Krperimental Biology*, 2010, 48: 258-264.

The absorbance was then measured using a microplate multi-well reader (Bio-Rad Laboratories Inc., model 3350, Hercules, Calif., USA) at 595 nm and a reference wavelength of 620 nm. A statistical significance was tested between samples and negative control (cells with vehicle) using independent t-test by SPSS 11 program. DMSO is the vehicle used for dissolution of plant extracts and its final concentration on the cells was less than 0.2%. The percentage of change in viability was calculated according to the formula:

((Reading of extract/Reading of negative control)−1)×100.

A probit analysis was carried for $IC_{50}$ and $IC_{90}$ determination using SPSS 11 program; Bassyouni F. A., Abu-Baker S. M., Mahmoud K., Moharam M., El-Nakkady S. S., Abdel-Rehim M. (2014): Synthesis and biological evaluation of some new triazolo[1,5-a]quinoline derivatives as anticancer and antimicrobial agents". RSC Advances 4(46): 24131-24141.

Cytotoxic Effect on Human Cell Lines.

Cell viability was assessed by the mitochondrial dependent reduction of yellow MTT (3-(4,5-dimethylthiazol-2-yl)-2,5-diphenyl tetrazolium bromide) to purple formazan; Mossman, et al., id. (1983).

All procedures were done in a sterile area using a Laminar flow cabinet biosafety class II level (Baker, SG403INT, Sanford, Me., USA). Cells were suspended in RPMI 1640 medium for HePG2, MCF7 and HCT116 and DMEM for A549 and PC3, 1% antibiotic-antimycotic mixture (10,000 U/ml Potassium Penicillin, 10,000 µg/ml Streptomycin Sulfate and 25 µg/ml Amphotericin B) and 1% L-glutamine at 37° C. under 5% $CO_2$.

Cells were batch cultured for 10 days, then seeded at concentration of 10×103 cells/well in fresh complete growth medium in 96-well microtiter plastic plates at 37° C. for 24 h under 5% $CO_2$ using a water jacketed Carbon dioxide incubator (Sheldon, TC2323, Cornelius, Oreg., USA). Media was aspirated, fresh medium (without serum) was added and cells were incubated either alone (negative control) or with different concentrations of sample to give a final concentration of 100, 50, 25, 12.5, 6.25, 3.125, 1.56 and 0.78 µg/ml. After 48 h of incubation, medium was aspirated, 40 µl MTT salt (2.5 µg/ml) were added to each well and incubated for further four hours at 37° C. under 5% $CO_2$. To stop the reaction and dissolving the formed crystals, 200 µL of 10% Sodium dodecyl sulphate (SDS) in deionized water was added to each well and incubated overnight at 37° C. A positive control which composed of 100 µg/ml was used as a known cytotoxic natural agent who gives 100% lethality under the same conditions; Thabrew, et al., id. (1997); El-Menshawi, et al., id. (2010).

The absorbance was then measured using a microplate multi-well reader (Bio-Rad Laboratories Inc., model 3350, Hercules, Calif., USA) at 595 nm and a reference wavelength of 620 nm. A statistical significance was tested between samples and negative control (cells with vehicle) using independent t-test by SPSS 11 program. DMSO is the vehicle used for dissolution of plant extracts and its final concentration on the cells was less than 0.2%. The percentage of change in viability was calculated according to the formula:

((Reading of extract/Reading of negative control)−1)×100.

A probit analysis was carried for IC50 and IC90 determination using SPSS 11 program; Bassyouni F. A., Abu-Baker S. M., Mahmoud K., Moharam M., El-Nakkady S. S., Abdel-Rehim M. (2014): Synthesis and biological evaluation of some new triazolo[1,5-a]quinoline derivatives as anticancer and antimicrobial agents". RSC Advances 4(46): 24131-24141.

Data Analysis of Cytotoxic Activity Test. Sample Testing Against the Normal Human Epithelial Cell Line: BJ1 (Normal Skin Fibroblast).

Sample concentrations range between (100 to 0.78 µg/ml) using a MIT assay. Table 1 shows the effect of compound 1 on the normal skin fibroblast in which show more safe in which affect cells at higher concentration 100 ppm.

TABLE 1

| Sample Code | $IC_{50}$ (µg/ml) | $IC_{90}$ (µg/ml) | Remarks |
|---|---|---|---|
| Compound 1 | — | — | 41.5% at 100 ppm |
| Compound 2 | 16.9 | 29.1 | 100% at 100 ppm |
| Compound 3 | 61.0 | 105.0 | 80% at 100 ppm |
| DMSO | — | — | 1% at 100 ppm |
| Negative control | — | — | 0% |

$IC_{50}$: Lethal concentration of the sample which causes the death of 50% of cells in 48 hrs
$IC_{90}$: Lethal 1 concentration of the sample which causes the death of 90% of cells in 48 hrs Samples Tested Against the Human Tumor Cell Line(s): HePG 2 a Human Hepatocellular Carcinoma Cell Line.

Sample concentration ranged between 100 down to 0.78 µg/ml using MTT assay.

TABLE 2

Cytotoxic activity of Compounds 1, 2 and 3 against the hepatocellular carcinoma cell line HEPG2.

| Sample Code | $IC_{50}$ (µg/ml) | $IC_{90}$ (µg/ml) | Remarks |
|---|---|---|---|
| Compound 1 | 45.5 | 77.3 | 95.3% at 100 ppm |
| Compound 2 | 15.7 | 28.3 | 100% at 100 ppm |
| Compound 3 | 14.7 | 26.0 | 100% at 100 ppm |
| DMSO | — | — | 1% at 100 ppm |
| Negative control | — | — | 0% |

$IC_{50}$: Lethal concentration of the sample which causes the death of 50% of cells in 48 hrs
$IC_{90}$: Lethal concentration of the sample which causes the death of 90% of cells in 48 hrs Table 2 above shows that although the $IC_{50}$ and the $IC_{90}$ of Compound 1 was higher than Compound 2 and Compound 3, Compound 1 was safer as indicated from its effect on normal cells (Table 1).

Table 3 Shows the Cytotoxic Activity of the Doxorubicin Against the Hepatocellular Carcinoma Cell Line HEPG2

TABLE 3

Positive control Adriamycin (Doxorubicin) [Mw = 579.99]

|  | $IC_{50}$ µg/ml | $IC_{50}$ µM |
|---|---|---|
| Doxorubicin | 21.6 | 37.8 |

Terminology

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A compound of formula I:

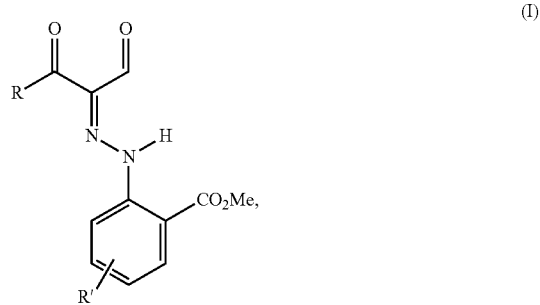

wherein R is $C_2$-$C_6$ alkyl or substituted 2-thienyl
R' is hydrogen or unsubstituted or substituted alkyl, alkenyl, alkynyl or aryl.

2. The compound of claim 1, wherein R is $C_2$-$C_6$ alkyl.

3. The compound of claim 1, wherein R is substituted 2-thienyl.

4. A composition comprising a compound of formula I and a sterile pharmaceutically acceptable carrier, excipient or solvent; wherein said compound of formula I is:

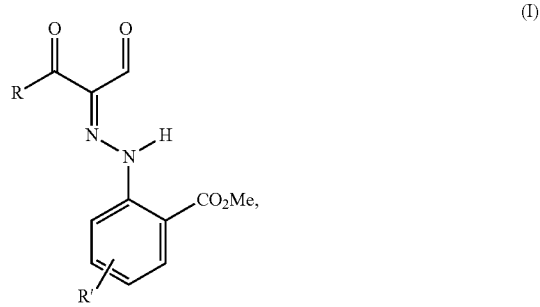

wherein R is an unsubstituted or substituted alkyl, aryl, or a 5- or 6-membered ring containing at least one nitrogen, oxygen or sulfur atom and R' is hydrogen or unsubstituted or substituted alkyl, alkenyl, alkynyl or aryl.

5. The composition of claim 4, wherein the pharmaceutically acceptable carrier is a liposome or a PEGylated liposome.

6. The composition of claim 4, further comprising at least one P glycoprotein inhibitor selected from the group consisting of amiodarone, clarithromycin, ciclosporin, colchicine, diltiazem, erythromycin, felodipine, lansoprazole, and omeprazole; and/or at least one proton-pump inhibitor selected from the group consisting of nifedipine, paroxetine, sertraline, quinidine, tamoxifen and verapamil; and/or at least one of Sorafenib, 5-flurouracil, doxorubicin, or Regorafenib.

7. A method for treating a human subject having hepatocellular carcinoma comprising administering an effective amount of a compound of formula I to the subject:

wherein said compound of formula I is:

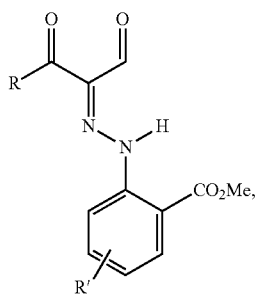

(I)

wherein R is an unsubstituted or substituted alkyl, aryl, or a 5- or 6-membered ring containing at least one nitrogen, oxygen or sulfur atom and R' is hydrogen or unsubstituted or substituted alkyl, alkenyl, alkynyl or aryl.

8. The method of claim 7, wherein in said compound of formula I, R is methyl.

9. The method of claim 7, wherein in said compound of formula I, R is $C_2$-$C_6$ alkyl.

10. The method of claim 7, wherein in said compound of formula I, R is phenyl.

11. The method of claim 7, wherein in said compound of formula I, R is 2-thienyl.

12. The method of claim 7, further comprising treating the human subject by surgery.

13. The method of claim 7, further comprising treating the human subject with radiation therapy.

14. The method of claim 7, further comprising treating the human subject with at least one other chemotherapeutic agent or immunotherapy.

15. The method of claim 7, further comprising treating the human subject for hepatitis B or hepatitis C.

16. The method of claim 7, further comprising treating the human subject for alcoholism or cirrhosis.

17. The method of claim 7, further comprising treating the human subject for obesity, diabetes, iron storage disease, or exposure to aflatoxin.

* * * * *